United States Patent [19]

Ahlman et al.

[11] Patent Number: 5,331,013

[45] Date of Patent: Jul. 19, 1994

[54] METHOD FOR THE TREATMENT OF ULCERATIVE PROCTITIS AND COLITIS

[75] Inventors: B. Håkan J. Ahlman, Askim; Stellan Björck, Hovås; Annica B. Dahlström, Askim, all of Sweden

[73] Assignee: Aktiebolaget Astra, Sodertalje, Sweden

[21] Appl. No.: 860,278

[22] Filed: Apr. 1, 1992

Related U.S. Application Data

[63] Continuation of Ser. No. 646,505, Jan. 23, 1991, abandoned, which is a continuation of Ser. No. 363,097, Jun. 8, 1989, abandoned.

[51] Int. Cl.$^5$ .............................................. A61K 31/16
[52] U.S. Cl. .................................. 514/626; 514/817; 514/818
[58] Field of Search ....................... 514/626, 817, 818

[56] References Cited

U.S. PATENT DOCUMENTS

| 4,137,327 | 1/1979 | Marshall | 514/616 |
| 4,447,437 | 5/1984 | Ohnishi et al. | 514/284 |

OTHER PUBLICATIONS

Handbook of Nonprescription Drugs, 5th ed., 1977, Amer. Pharm. Assoc., Wash., D.C., pp. 67–69.
S. Bjorck, et al., Lignocaine and Ulcerative Proctitis, The Lancet Journal, Jun. 11, 1988, p. 1330.

*Primary Examiner*—Marianne M. Cintins
*Assistant Examiner*—Kimberly R. Jordan
*Attorney, Agent, or Firm*—White & Case

[57] ABSTRACT

A method for treatment of ulcerative colitis (and sequelae to surgically treated colitis, for instance ileal pouchiris) and ulcerative proctitis comprising administration to a patient suffering therefrom of a therapeutically effective amount of a local anaesthetic or a pharmaceutically acceptable salt thereof, preferably lidocaine hydrochloride in the form of a pharmaceutically acceptable preparation.

5 Claims, No Drawings

METHOD FOR THE TREATMENT OF ULCERATIVE PROCTITIS AND COLITIS

This application is a continuation of application Ser. No. 07/646,505, filed on Jan. 23, 1991, now abandoned, which is a continuation of U.S. Ser. No. 07/363,097 filed Jun. 8, 1989 (Abandoned).

FIELD OF THE INVENTION

The present invention is related to a method for the treatment of ulcerdrive proctitis and colitis, wherein a local anaesthetic e,g, lidocaine or a pharmaceutically acceptable salt thereof is administered rectally.

BACKGROUND OF THE INVENTION

Non-specific proctitis is considered to be a localized form of ulcerdrive colitis with identical histopathological findings (cf. Dennard-Jones, J E et al, Gut 1962, 3, p. 201–208). Ulcerative colitis always starts with rectal inflammation, but only one tenth of the proctitis patients will develop colohio disease. Recently damage and regeneration of peptide-containing neurons were observed in ulcerdrive colitis, suggesting damage of these neurons as a primary event (cf, Koch T R et al, Inflammatory Bowel Disease: Current status and future approach. Elsevier Science Publishers BV 1988, p. 25–30). Relatively few studies on inflammatory bowel disease have dealt with the influence of stress on intestinal function at the cellular level. Hyperplasia of the mucosal adrenergic innervation and reduction of the number of rectal enterochromaffin cells were first demonstrated in ulcerdrive colitis by Kyöola et al in Scand J Gastroent. 1977, 12, p. 363–367 using the Hillarp-Falck technique (cf. Corrodi H., Jonsson Cr., S. Histochem Cytochem 1967, 15, p. 65–78). Lymphocytes and plasma cells accumulate in the lamina proprid and together with polymorphnuclear cells crypt abscesses may form. Subsets of lymphocytes invade the inflamed mucosa, i.e. the suppressor-cytotoxic phenotype, (OKT$_8$), resides within the epithelium and the helper phenotype ( OKT$_4$), within the proprid (cf. Selby W S et al., Gut 1984, 25, p. 32–40).

PRIOR ART

Patients suffering from ulcerative colitis and proctitis are usually treated with different types of non-surgical therapy such as salazopyrin, corticosteroids and antibiotics alone or in combination. If this kind of therapy is without success the patients have earlier been treated surgically with colectomy.

OUTLINE OF THE INVENTION

It has now been clinically shown that the rectal administration of lidocaine hydrochloride in the form of a gel to patients suffering from ulcerdrive colitis and proctitis has resulted in restoration of mucosal integrity accompanied by depletion of OKT$_4$ and OKT$_8$ lymphocytes from the mucosa.

PHARMACEUTICAL PREPARATIONS

Lidocaine can be administered in a pharmaceutical preparation containing 0.5–5% of lidocaine, for instance in the form of a gel. This contains lidocaine hydrochloride anhydrous, hypromellos, sodium hydroxide, acid hydrochloride, conservans (methyl- and propylparaben) together with water for instillation. It is essential that the preparation does not contain antiseptics such as chlorhexidine or the like, as these kinds of compounds cause irrigative effects.

ULCERATIVE PROCTITIS/COLITIS

Depending on the extent of the disease the amounts given has been varied. 20 m) with 400 mg of lidocaine hydrochloride in each 20 ml volume, given twice daily, has been found to be sufficient to treat exquisite proctitis (extending to 16 cm above the dentate line) or distal procto-sigmoiditis, To treat inflammation engaging the whole of the procto-sigmoid area 50 ml of the preparation has been needed, and for left-Sided colitis 100 ml of preparation, still with a total of 800 mg of lidocaine hydrochloride amhydride per two doses was necessary. By inclusion of barium in the preparation, it has been found that the preparation spreads proximally to the splenic flexure when 100 ml is administered.

The lidocaine preparation can be administered intra-rectally with any suitable type of syringe that can bring the preparation into the rectum. From here the preparation is spread upwards by the movements of the intestine, to a level which is depending on the volume administered.

In patients surgically treated for ulcerative colitis with colectomy with construction of an ileal reservoir (a so called pouch), this pouch frequently becomes the site of the same type of inflammatory disease as the removed colon. This sequelae to surgically treated ulcerdrive colitis is called "ileal pouchiris" and can be treated with locally administered lidocaine.

Pharmacological Effect and Detailed Description of the Invention

Patients

Twenty-one consecutive patients (13 women and 8 men) with histopathologically proven ulcerative proctitis (UP)/procto-sigmoiditis (PS) were treated with topical lidocaine. The average age at referral among the women was 39±7 years and among the men 53±11 years; of the women 8 had UP and 5 had PS, of the men 4 had UP and 4 had PS. The previous history and stage of disease according to Truelove et al. Brit. Med. J. 1962, 2, p. 1708–1711 is given in Table 1 below. Earlier treatment for UP/PS included periods (1–3 weeks) of cotrison enemas and/or sulfasalazine (2–4 g per day). All such treatment was stopped in the patients 10–14 days prior to treatment with lidocaine preparation.

TABLE 1

| CLINICAL FINDINGS IN PATIENTS WITH UP/PS | | |
|---|---|---|
| | 13 women | 8 men |
| Duration of disease | <1 year 7 pts | <1 year 4 pts<br>>1 year 4 pts (2–15 years) |
| Previous attacks/earlier treatment | 9 pts | 5 pts |
| First attack | 5 pts | 3 pts |
| Severity of disease: | | |
| mild | 3 pts | — |
| moderate | 10 pts | 8 pts |

Clinical Examination

Endoscopy with biopsies was performed before and during treatment at regular intervals (3–6 weeks) and the inflammatory response and extent of disease were determined. The mucosal appearance was carefully examined with respect to ulcers, spontaneous or contact bleeding, mucus and pus. In the healing mucosa submucosal vessels were clearly observed. Rectal biopsies were taken at a level 10 cm proximal to the dentate line.

Treatment

The lidocaine preparation with the composition described above was applied intrarectally in a total dose of 800 mg per day until specific lymphocyte infiltration disappeared. The duration of treatment has varied between 3–8 weeks.

Histochemical Procedures

The rectal biopsies from all patients, taken before onset of treatment and repeatedly thereafter, were studied immunocytochemically.

Clinical Results of Treatment

Symptoms

None of the patients complained about any side effects of the treatment. All patients experienced a decreased rectal irritability within 2–4 days. Usually patients with UP have no changed bowel habits, while patients with PS have an increased number of bowel movements. The frequency decreased within 1–3 weeks to become normalized. In parallel with this normalisation the discharge of pus, blood and mucus with each bowel movement disappeared completely. In all UP patients such discharge disappeared within two weeks after onset of treatment.

Endoscopic Evaluation

In all patients with UP/PS a pale mucosa covered by highly viscid mucus was observed after one week of treatment. However, the mucosa was still fragile with contact bleeding upon touch. No touch bleeding was seen after 2–3 weeks. The submucosal vessels were clearly visible after 4–5 weeks.

Discussion

The first consecutive 21 patients all responded well to the treatment with lidocaine, and they were treated until no or very few $OKT_4$ and $OKT_8$ lymphocytes were seen extravasally in their biopsies. The patients were symptom-free and had a normal mucosa at endoscopy several weeks prior to such depletion was verified immunocytochemically.

In conclusion, topical treatment during a period of 3–8 weeks of the rectum and distal colon with lidocaine in patients with UP/PS has resulted in a rapid decrease of subjective and objective symptoms (which have been observed proctoscopically and morphologically in immunoincubated biopsis).

So far almost 100 patients have been treated with the method according to the invention. Out of these many young patients, who were listed for surgical treatment with colectomy as the "last alternative" have been successfully treated. A maximum of 800 mg. of lidocaine hydrochloride has been given.

We claim:

1. A method for restoring mucosol integrity in a patient suffering from ulcerative proctitis and ulcerative colitis comprising local administration to the reactal/-colonic mucosa of the patient of an effective amount of a composition comprising a local anaesthetic or a pharmaceutically acceptable salt thereof and wherein the composition does not contain antiseptics which cause irrigative effects.

2. A method for restoring mucosal integrity in a surgically treated ulcerative colitis patient suffering from ileal pouchitis comprising local administration to the rectal/colonic mucosa of the patient of an effective amount of a composition comprising a local anaesthetic or a pharmaceutically acceptable salt thereof.

3. A method according to claim 1 or 2, wherein the local anaesthetic is lidocaine or a pharmaceutically acceptable salt thereof.

4. A method according to claim 3, wherein the local anaesthetic is lidocaine hydrochloride.

5. A method according to claim 3, wherein lidocaine is administered in the form of a pharmaceutically acceptable form.

* * * * *

UNITED STATES PATENT AND TRADEMARK OFFICE
CERTIFICATE OF CORRECTION

PATENT NO. : 5,331,013
DATED : July 19, 1994
INVENTOR(S) : Ahlman et al.

It is certified that error appears in the above-indentified patent and that said Letters Patent is hereby corrected as shown below:

col. 1, lines 18, 33 and 56 and col. 2, lines 28-29, change "ulcerdrive" to --ulcerative--;

col. 1, line 22, change "colohio" to --colonic--;

col. 1, line 33, change "Kyöola" to --Kyösola--;

col. 1, lines 37 and 42, change "propid" to --propia--;

col. 2, line 6, change "m)" to --ml--;

col. 2, line 14, change "amhydride" to --anhydride--;

col. 2, line 29, change "pouchiris" to --pouchitis--;

col. 2, line 46, change "cotrison" to --cortison--;

col. 4, line 32, after "thereof," insert --and wherein the composition does not contain antiseptics which cause irrigative effects--.

Signed and Sealed this

Tenth Day of February, 1998

*Attest:*

BRUCE LEHMAN

*Attesting Officer*     *Commissioner of Patents and Trademarks*